US00PP21014P3

(12) United States Plant Patent
Kawashima et al.

(10) Patent No.: US PP21,014 P3
(45) Date of Patent: May 25, 2010

(54) **NEW GUINEA *IMPATIENS* PLANT NAMED 'SAKIMP008'**

(50) Latin Name: *Impatiens×hybrida*
Varietal Denomination: SAKIMP008

(75) Inventors: Moriya Kawashima, Yokohama (JP); Yoneo Kobayashi, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/288,738

(22) Filed: Oct. 23, 2008

(65) Prior Publication Data

US 2010/0107290 P1 Apr. 29, 2010

(51) Int. Cl.
*A01H 5/00* (2006.01)

(52) U.S. Cl. ..... Plt./318.3

(58) Field of Classification Search ..... Plt./318.3
See application file for complete search history.

*Primary Examiner*—June Hwu
(74) *Attorney, Agent, or Firm*—Jondle & Associates, P.C.

(57) ABSTRACT

A New Guinea *Impatiens* plant particularly distinguished by having salmon-orange flowers, a mounding growth habit, and strong rooting is disclosed.

1 Drawing Sheet

Genus and species: *Impatiens×hybrida.*
Variety denomination: 'SAKIMP008'.

BACKGROUND OF THE NEW PLANT

The present invention comprises of a new and distinct cultivar of New Guinea *Impatiens*, botanically known as *Impatiens×hybrida,* and referred to by the variety name 'SAKIMP008'. 'SAKIMP008' originated from an interspecific hybridization between the female *Impatiens* plant 'NG-02SM-1', an unpatented proprietary *Impatiens* breeding line with a deep, orange flower color, medium flower size and mounding plant growth habit and the male *Impatiens* plant 'NC-229', an unpatented proprietary *Impatiens* breeding line with a magenta flower color, medium flower size and erect plant growth habit, in Misato, Japan.

In January 2004, the female parent line 'NG-02SM-1' and male parent line 'NC-229' were crossed and a population of $F_1$ plants was created. The $F_1$ plants were evaluated in Misato, Japan in an open field trial. The criteria for plant selection included salmon flower color, strong root system and mounding plant growth habit. At the completion of the trial, one single-plant selection was made based on the above criteria and vegetatively propagated. From May to August 2005, the selection was evaluated in an open field in Misato, Japan.

Shoot-tip cuttings of the variety were then shipped to Salinas, Calif., where the plants were regenerated and reevaluated for stability of traits. The selection subsequently was named 'SAKIMP008' and found to have its unique characteristics reproduced true to type in successive generations of asexual propagation via vegetative cuttings in Salinas, Calif.

SUMMARY OF THE INVENTION

The following are the most outstanding and distinguishing characteristics of this new cultivar when grown under normal horticultural practices in Salinas, Calif.

1. Salmon-orange flowers;
2. Mounding growth habit; and
3. Strong rooting.

DESCRIPTION OF THE PHOTOGRAPHS

This new *impatiens* plant is illustrated by the accompanying photographs which show the overall plant habit including blooms, buds, and foliage of the plant; the colors shown are as true as can be reasonably obtained by conventional photographic procedures. The photographs are of plants that are 4 months from propagation by terminal cutting in Salinas, Calif., under greenhouse conditions.

DETAILED DESCRIPTION OF THE NEW CULTIVAR

Figure 1:
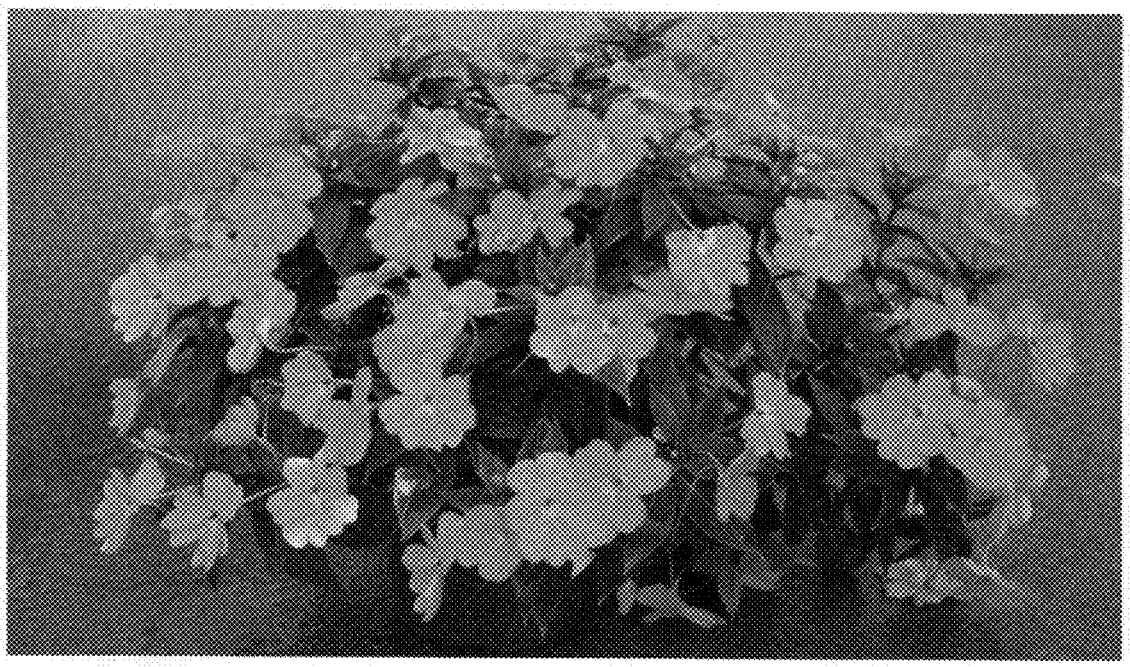
FIG. 1 shows overall plant habit including blooms, buds and foliage.
Figure 2:
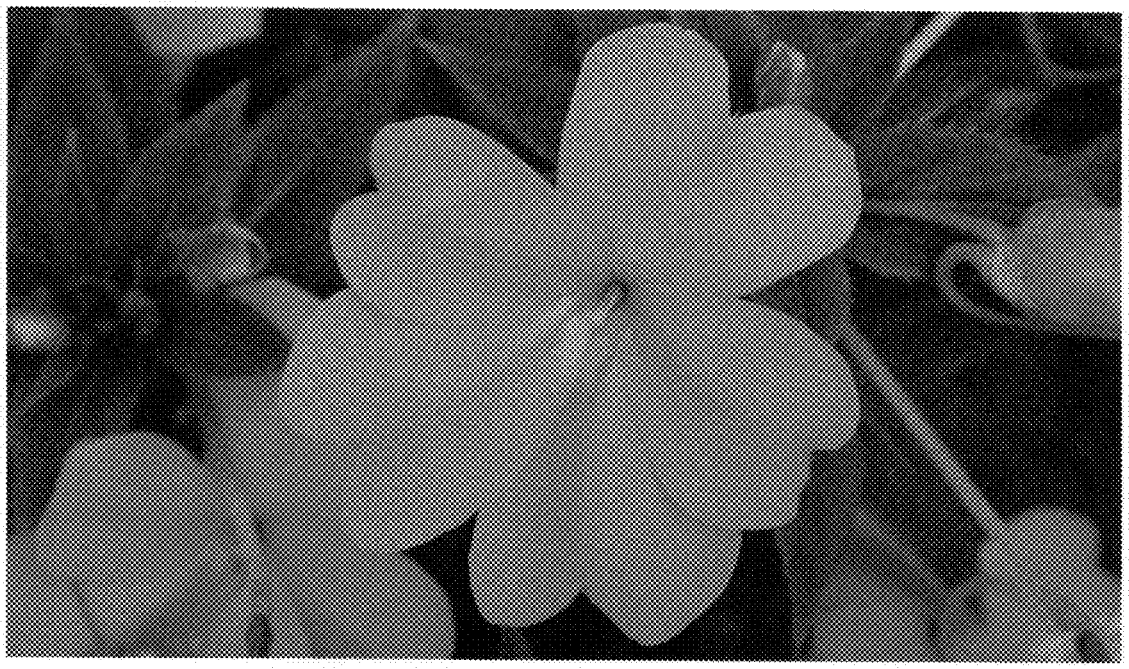
FIG. 2 shows the mature inflorescence.

The following detailed descriptions set forth the distinctive characteristics of 'SAKIMP008'. The data which define these characteristics were collected from asexual reproductions carried out in Salinas, Calif. The plant history was taken on plants grown for about four months from propagation by terminal cuttings under greenhouse conditions. Color references are primarily to the R.H.S. Colour Chart of The Royal Horticultural Society of London (R.H.S.), 4$^{th}$ edition (2001). Anatomic labels are from *The Cambridge Illustrated Glossary of Botanical Terms,* by M. Hickey and C. King, Cambridge University Press.

DETAILED BOTANICAL DESCRIPTION

Classification:

*Family.*—Balsaminaceae.
*Botanical.*—*Impatiens×hybrida.*
*Common name.*—*Impatiens.*

Parentage:

*Female parent.*—'NG-02SM-1', an unpatented proprietary deep, dark orange flowered *Impatiens* plant.
*Male parent.*—'NC-229', an unpatented proprietary magenta flowered *Impatiens* plant.

Growth:

*Time to produce a rooted cutting.*—The terminal 1.0 to 1.5 inches of an actively growing stem was excised. The vegetative cuttings were propagated in five to six weeks. The base of each cutting was dipped for 1 to 2 seconds in a 1:9 solution of Dip 'N Grow (1 solution:

9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2–3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant description:

*Habit.*—Mounding.

*Life cycle.*—Tender perennial.

*Height.*—25.0 cm to 26.0 cm from soil line to top of foliage.

*Spread.*—57.0 cm to 58.0 cm.

*Time to produce a rooted cutting.*—4 weeks.

*Flowering requirements.*—Will flower so long as temperature is above 5° C.

*Temperature tolerance.*—Plants have been observed to continuously flower at a temperature range of 5° C. to 36° C.; plants can withstand high heat and humidity.

Branches:

*Number.*—12 total with 4 main branches.

*Length.*—Approximately 2.0 cm from soil line to first node; approximately 18.0 cm to 20.0 cm total.

*Diameter (main branch).*—1.0 cm to 1.2 cm.

*Color.*—RHS 187B (Greyed-Purple).

Stems:

*Length.*—8.0 cm from first to second node; 13.0 cm to 14.0 cm total length.

*Diameter.*—0.6 cm to 0.7 cm.

*Internode length.*—2.2 cm to 2.3 cm.

*Color.*—RHS 187B (Greyed-Purple).

*Stem description.*—Strong; circular cross-section, smooth and shiny.

*Pubescence.*—Absent.

*Anthocyanin color.*—RHS 187B (Greyed-purple).

Leaves:

*Arrangement.*—Whorled with up to 5 leaves per node, opposite if only two leaves at one node.

*Length.*—8.0 cm to 8.5 cm.

*Width.*—2.8 cm to 3.0 cm.

*Shape.*—Lanceolate, curled.

*Margin.*—Ciliate.

*Apex.*—Acuminate.

*Base.*—Attenuate.

*Texture.*—Dull; waxy.

*Color.*—Upper surface: RHS 147A (Yellow-green). Lower surface: RHS 147B (Yellow-green).

*Fragrance.*—Absent.

*Pubescence (both surfaces).*—Absent.

*Variegation.*—Absent.

*Venation.*—Pinnate.

*Venation color.*—Upper surface: RHS 147D (Yellow-green). Lower surface: RHS 185C (Greyed-purple).

*Petioles.*—Length: 0.5 cm to 1.0 cm. Diameter: 0.2 cm to 0.3 cm. Color: RHS 185C (Greyed-purple). Texture: Smooth, glabrous.

Flower buds:

*Shape.*—Deltoid, longitudinal cross-section.

*Length.*—2.2 cm.

*Diameter.*—1.3 cm.

*Color.*—RHS 50A (Red).

*Texture.*—Glabrous.

Inflorescence:

*Blooming habit.*—Will flower as long as the temperature is above 5° C.

*Inflorescence type.*—Single flower with spur.

*Number of flowers per node.*—1 to 3 in bloom at one time; about 4 to 6 flower buds.

*Number of flowers per plant.*—Approximately 110 in bloom.

*Lastingness of individual blooms on the plant.*—14 days.

*Fragrance.*—Absent.

Peduncles:

*Length.*—4.5 cm to 5.0 cm.

*Diameter.*—0.18 cm to 0.20 cm.

*Color.*—RHS 146D (Yellow-green).

*Texture.*—Smooth, glabrous.

Corolla:

*Shape.*—Roughly circular with 5 radial petals.

*Diameter.*—About 6.0 cm to 6.2 cm.

*Depth.*—0.2 cm.

Petals:

*Shape.*—Obcordate.

*Length.*—3.5 cm.

*Width.*—2.5 cm.

*Apex.*—Emarginate (cleaved).

*Base.*—Attenuate.

*Margin.*—Entire.

*Texture.*—Glabrous.

*Color.*—Upper surface: RHS 40A (Red). Lower surface: RHS 47C (Red). Eye zone: RHS 55B (Red).

Spur:

*Shape.*—Tubular and curved downward.

*Color.*—RHS 47B (Red).

*Length.*—5.5. cm.

*Diameter.*—0.2 cm.

Sepals:

*Shape.*—Lanceolate.

*Number.*—Two.

*Color.*—RHS N144D (Yellow-green).

*Length.*—1.2 cm.

*Diameter.*—0.5 cm.

*Apex.*—Caudate.

*Base.*—Subcordate.

*Margin.*—Entire.

*Texture.*—Glabrous.

Reproductive organs:

*Stamens.*—Form: Fused; split into 4 lobes. Number: Many. Filament length: 0.4 cm. Filament color: RHS 50B (Red). Anther length: 0.5 cm. Anther color: RHS N155A (White). Pollen amount: Abundant. Pollen color: RHS N155A (White). Pollen description: Powdery.

*Pistil.*—Number: 5. Stigma color: RHS 137A (Green). Style color: RHS 137A (Green). Style length: 0.7 cm.

*Ovary arrangement.*—Parietal.

*Ovary surface color.*—RHS 147A (Yellow-green).

Fruit and seed set: No seed set observed.

Disease and insect resistance: No particular resistance or susceptibility has been observed.

COMPARISON WITH PARENTAL AND COMMERCIAL CULTIVARS

'SAKIMP008' is similar to the female parent 'NG-02SM-1' and the male parent 'NC-229', however, there are differences as listed in the table below:

TABLE 1

Comparison of Characteristics between 'SAKIMP008' and parental cultivars

| Characteristic | 'SAKIMP008' | Male Parent 'NC-229' | Female Parent 'NG-02SM-1' |
|---|---|---|---|
| Flower color | Salmon Orange | Magenta | Deep Orange |
| Plant growth habit | Mounding | Mounding | Erect |

'SAKIMP008' is similar to the commercial *Impatiens* variety 'Misato FG2' (U.S. Plant Pat. No. 17,663) (known commercially as 'SunPatiens Orange') however, there are differences as listed in Table 2 below:

TABLE 2

Comparison of Characteristics between 'SAKIMP008' and 'Misato FG2'

| Characteristic | 'SAKIMP008' | 'Misato FG2' |
|---|---|---|
| Growth habit | Mounding | Upright |
| Petal color, upper surface | RHS 40A (Red) | RHS N30C (Orange-Red) |
| Spur color | RHS 47B (Red) | RHS 63A (Red-Purple) at base fading to RHS 62D (Red-Purple) at tip |

I claim:

1. A new and distinct cultivar of New Guinea *Impatiens* plant as shown and described herein.

* * * * *